Feb. 6, 1973 R. SUMRULD Plant Pat. 3,297
PLUM TREE
Filed July 27, 1971
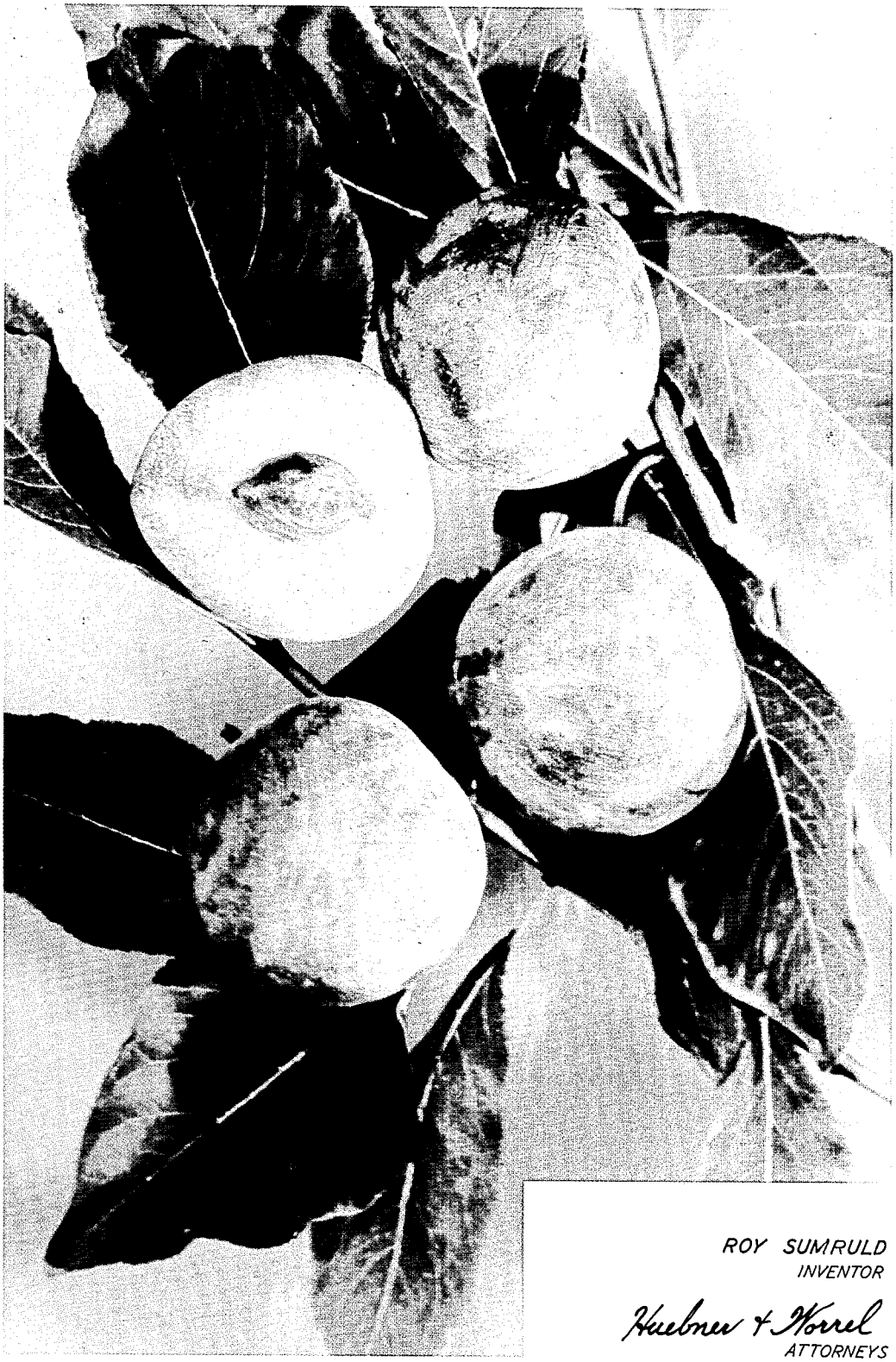
ROY SUMRULD
INVENTOR
Huebner & Worrel
ATTORNEYS

United States Patent Office

Plant Pat. 3,297

Patented Feb. 6, 1973

3,297

PLUM TREE

Roy Sumruld, 2957 E. Tulare Ave., Tulare, Calif. 93274

Filed July 27, 1971, Ser. No. 166,648

Claims priority, application Netherlands, Aug. 25, 1970, 7012597

Int. Cl. A01h *5/03*

U.S. Cl. Plt.—38 1 Claim

ABSTRACT OF THE DISCLOSURE

A plum tree which is generally similar to the unpatented Santa Rosa plum tree but which bears fruit which ripens approximately three months later than that of the Santa Rosa.

BACKGROUND

The present invention relates to a plum tree and more particularly to a plum tree which produces fruit generally similar to that of the Santa Rosa plum tree (unpatented), which it most nearly resembles, but which ripens approximately three months later.

In the marketing of fresh fruit and other produce, it is not only desirable to offer a high quality product but, if a maximum return for the product is to be received, to market it when there is minimum competition for such products. While some harvesting control can be exercised over most vegetables by regulating their time of planting, the time of harvest for most tree fruits cannot be regulated by the farmer to any appreciable extent. Thus, almost all the fruits of a given variety produced under the same or similar climatic and soil conditions are marketed at about the same time and because of the excess supply and no appreciable increase in demand, the prices thereof are automatically depressed. In view of this, it has become increasingly important to develop varieties of fruit trees which produce high quality fruit in advance of, or subsequent to, similar varieties. Success in such development has led to a substantial lengthening of the harvest seasons for plums, apricots, peaches, nectarines, grapes and the like.

Thus, it is frequently a prime objective of plant breeders to develop or discover new and improved fruit trees which not only produce new and improved varieties of fruit but which, by their unique times of harvest, have particular commercial value.

Pursuant to this objective, I planted a number of plum seeds on my ranch at 2927 East Tulare Avenue, Tulare, Calif., germinated the seeds, and cared for the resulting seedlings until they produced a crop. In September or October of 1965 I noted the superior characteristics of the instant variety plum tree grown from such a seedling. The parentage of the seedling is unknown but is believed to be a seed from a Santa Rosa plum tree of open-pollination. I continued to observe this plum tree and in February 1967 asexually reproduced it by grafting scions thereof into my plum orchard on my ranch at 2927 East Tulare Avenue, Tulare, Calif. The plum trees thus asexually reproduced have been observed during succeeding years and have proved to have the same characteristics as those originally noted for the seedling.

The following is a detailed description of my new variety of plum tree as observed on my designated ranch with color terminology in accordance with the Nickerson Color Fan published by Munsell Color Co., Inc., distributed by the American Horticultural Society of 1600 Bladensburg Road, NE., Washington, D.C., except where general color terms of ordinary significance are obvious.

*Tree*

Medium size, vigorous growth, dense, upright, vase form preferably pruned to open vase shape, hardy, productive and regular bearer requiring thinning to achieve desired size. Similar to the Santa Rosa plum tree in the foregoing respects.

*Trunk*

Medium, smooth, dull brown with lenticels similar to the Santa Rosa plum tree.

*Branches*

Generally vigorous varying in color from the brown of the trunk to the light green of 10 Y 5/5 on the new growth.

*Leaves*

Large, oblong-lanceolate to oblanceolate, margins crenate to repand, selected from mid-portions of vigorous unbranched terminal shoots from 4¼ to 4½ inches in length and from 2 to 2⅛ inches in width, on the average somewhat longer than the leaves of the Santa Rosa plum tree, acutely pointed, of medium thickness similar to the Santa Rosa plum tree, medium green of 2.5 G 4/6, vein coloring light green, apex angle one inch from tip more than 45 and base angle ½ inch from petiole slightly more than 45°.

*Buds*

Approximately 5/16 inch long when ready to open, long-oval, smooth and satiny, petals white with light green sepals and calyx.

*Blossoms*

Usually bloom the second week of March under the conditions prevailing in the San Joaquin Valley of California, ¾ inch in diameter, chalk white, single pistil, with from 30–32 stamens.

*Fruit*

Maturity: Last week in September and first week in October.

Shape: Substantially uniform, spherical, 2 3/16 inches in the suture plane and transversely of the suture plane and from 2⅛ to 2 5/16 inches in length, round base, concave at stem, stem approximately ¾ inch in length with minimal adherence to the stone, short round blunt pistil point.

Skin: Tenacious, medium thick, medium tough, not astringent or bitter, no noted tendency to crack, yellow to greenish yellow overlayed with pink giving the general effect when ripe of relatively deep pink, 10 RP 6/12, moderate short down.

Flesh: Pale orange-yellow of 7.5 YR 9/4 to deep pink near skin of 10 RP 6/12, pit cavity approximately ½ inch deep and ⅝ inch wide of pale orange-yellow of 7.5 YR 9/4, moderate juice, firm and meaty, fine tender fibers, ripens evenly, mild flavor, slight aroma, good eating quality.

Stone: Cling, adhering to flesh over entire surface, fibers fairly long, length approximately 5/16 inch, breadth approximately ⅝ inch, thickness approximately ⅞ inch, ovoid having rounded base, rounded apex with short acute tip, symmetrical, relatively smooth surface with some slight bumpy irregularities, slight ridges extending longitudinally of the pit with thick ventral and dorsal edges having no wings, moderate brown of 7.5 YR 4/5 with no observable tendency to split.

Principal use: Fresh eating.

Keeping quality: Good.

Shipping quality: Good.

In substantially all of its characteristics except its ripening time, the subject variety is virtually identical to that of the Santa Rosa plum tree. This applies generally to its shape, size, vigor, color and fruit flavor, except that its leaves are somewhat longer and more pointed than those of the Santa Rosa, its fruit is slightly more pointed with slightly rougher surface and is perhaps a little less juicy but noticeably firmer and thus has superior shipping and keeping qualities. The fruit of the subject variety ripens in late September or early October approximately three months later than the fruit of the Santa Rosa.

Although the new variety of plum tree possesses the described characteristics under the growing conditions prevailing in Tulare County, in the central portion of the San Joaquin Valley, Calif., it is to be understood that variations of the usual magnitude in characteristics incident to differences in environment, growing conditions, fertilization, irrigation, pruning, thinning and pest control are to be expected.

Having thus described and illustrated my new variety of plum tree, what is claimed as new and desired to be secured by Letters Patent is:

1. A new and distinct variety of plum tree, substantially as herein shown and described, characterized particularly as to novelty by its substantial similarity to the unpatented Santa Rosa plum tree but bearing fruit which, although it is substantially identical to the fruit of the Santa Rosa plum tree, ripens approximately three months later than that of the Santa Rosa plum tree.

No references cited.

ROBERT E. BAGWILL, Primary Examiner